(12) United States Patent
Westcott et al.

(10) Patent No.: US 7,329,781 B2
(45) Date of Patent: Feb. 12, 2008

(54) METHODS OF PREPARING MAIN GROUP BORYL COMPOUNDS

(75) Inventors: Stephen A. Westcott, 299 Kinnear Road, Cormier-Village, New Brunswick (CA) E4P 5X9; Jonathan D. Webb, Quispamsis (CA); Daniel I. McIsaac, Mermaid (CA); Christopher M. Vogels, Sackville (CA)

(73) Assignee: Stephen A. Westcott, Cormier-Village (CA)

( * ) Notice: Subject to any disclaimer, the term of this patent is extended or adjusted under 35 U.S.C. 154(b) by 0 days.

(21) Appl. No.: 11/357,207

(22) Filed: Feb. 21, 2006

(65) Prior Publication Data

US 2006/0205966 A1 Sep. 14, 2006

Related U.S. Application Data

(60) Provisional application No. 60/655,427, filed on Feb. 24, 2005.

(51) Int. Cl.
 *C07F 5/02* (2006.01)
(52) U.S. Cl. ............................................. 568/1; 568/6
(58) Field of Classification Search .................. 568/1, 568/6, 7
See application file for complete search history.

(56) References Cited

U.S. PATENT DOCUMENTS 2,960,530 A 11/1960 Brotherton et al.
4,935,493 A * 6/1990 Bachovchin et al. ........ 530/331

OTHER PUBLICATIONS

Carter et al., Organometallics (2001), 20(11), 2130-2132.*
Mayer et al., Chemische Berichte (1992), 125(2), 401-5.*
Brown et al., Journal of Organic Chemistry (1989), 54(26), 6079-84.*
Ishiyama et al., J. Organometal. Chem. 680 (2003) 3-11).*
Hamilton et al., Journal of Organometallic Chemistry, 680, Aug. 29, 2003, pp. 143-147.*
Miyaura et al., Palladium-Catalyzed Cross-Coupling Reactions of Organoboron Compounds, Chem. Rev., 1995, 2457-2483, 95(7).
Trost et al., Nickel catalysed coupling of allylamines and boronic acids, J. Chem. Soc. Perkin Trans. 1, 1995, 2083-2096.
Chan et al., New N-and O-Arylations with Phenylboronic Acids and Cupric Acetate, Tetrahedron Letters, 1998, 2933-2936, 39.
Berrée et al., Synthesis of the marine sponge alkaiold oroidin and its analogues via Suzuki cross-coupling reactions, Tetrahedron Letters, 2002, 4935-4938, 43.
Sakuma et al., Rhodlum(I)-Catalyzed Asymmetric 1,4-Addition of Arylboronic Acids to α,β-Unsaturated Amides, J. Org. Chem., 2001, 8944-8946, 66(26).
Carboni et al., Boronic ester as a linker system for solid phase synthesis, Tetrahedron Letters, 1999, 7979-7983, 40.
Farfán et al., New perspectives for boronic esters in macrocyclic chemistry, Journal of Organometallic Chemistry, 1999, 70-81, 581.

(Continued)

*Primary Examiner*—Karl Puttlitz
(74) *Attorney, Agent, or Firm*—Bereskin & Parr; Patricia Folkins (57) ABSTRACT

The present invention relates to a method of preparing main group boryl compounds by reacting main group hydrides with hydroborating reagents in the presence of a transition metal catalyst.

25 Claims, 2 Drawing Sheets

OTHER PUBLICATIONS

Minutolo et al., Three-Component Synthesis of Substituted $\eta^5$-Cyclopentadienyltricarbonylrhenium Complexes: Scope, Limitations and Mechanistic Interpretations, Organometallics, 1999, 2519-2530, 18(13).

Matteson, D.S., α-Halo Boronic Esters in Asymmetric Synthesis, Tetrahedron, 1998, 10555-10607, 54.

Tailor et al., Tandem Aza[4+2]/Allylboration: A Novel Multicomponent Reaction for the Stereocontrolled Synthesis of α-Hydroxyalkyl Piperidine Derivatives, Organic Letters, 2000, 3716-3718, 2(33).

Petasis et al., Highly Stereocontrolled One-Step Synthesis of anti-β-Amino Alcohols from Organoboronic Acids, Amines, and α-Hydroxy Aldehdes, J. Am. Chem. Soc., 1998, 11798-11799, 120(45).

Batey et al., Alkenyl and Aryl Boronates-Mild Nucleophiles for the Stereoselective Formation of Functionalized N-Heterocycles, J. Am. Chem. Soc., 1999, 5075-5076, 121(21).

Yamamoto et al., Molecular Design of a PET-based Chemosensor for Uronic Acids and Sialic Acids Utilizing a Cooperative Action of Boronic Acid and Metal Chelate, Tetrahedron, 1998, 3125-3140, 54.

Eggert et al., A New Glucose-Selective Fluorescent Bisboronic Acid. First Report of Strong α-Furanose Complexation in Aqueous Solution at Physiological pH. J. Org. Chem., 1999, 3846-3852, 64(11).

Arimori et al., A D-glucose selective fluorescent assay, Tetrahedron Letters, 2002, 303-305, 43.

Wang et al., Curr. Org. Chem. 2002, 1285, 6. (not available).

James et al., Fluorescent saccharide receptors: a sweet solution to the design, assembly and evaluation of boronic acid derived PET sensors, Chem. Commun., 1996, 281-288.

Yang et al., Boronic Acid Compounds as Potential Pharmaceutical Agents, Medicinal Research Reviews, 2003, 346-368, 23(3).

Morin, C., Tetrahedron, 1994, 12521, 50. (not available).

Stoll et al., Differences in Binding Modes of Enantiomers of 1-Acetamido Boronic Acid Based Protease Inhibitors: Crystal Structures of γ-Chymotrypsin and Subtilisin Carlsberg Complexes, Biochemistry, 1998, 451-462, 37(2).

Coutts et al., Structure-Activity Relationships of Boronic Acid Inhibitors of Dipeptidyl Peptidase IV. 1. Variation of the $P_2$ Position of $X_{aa}$-boroPro Dipeptides, J. Med. Chem., 1996, 2087-2094, 39(10).

Priestley et al., 1-Aminocyclopropaneboronic Acid: Synthesis and Incorporation into an Inhibitor of Hepatitis C Virus NS3 Protease, Organic Letters, 2000, 3095-3097, 2(20).

Skordalakes et al., Crystallographic Structures of Human α-Thrombin Complexed to Peptide Boronic Acids Lacking a Positive Charge at P1. Evidence of Novel Interactions, J. Am. Chem. Soc., 1997, 9935-9936, 119(41).

Wiley et al., Phenylboronic Acid-Salicythydroxamic Acid Bioconjugates. 2. Polyvalent Immobilization of Protein Ligands for Affinity Chromatography, Bioconjugate Chem., 2001, 240-250, 12(2).

Jagannathan et al., Synthesis of Boronic Acid Analogues of α-Amino Acids by Introducing Side Chains as Electrophiles, J. Org. Chem, 2001, 6375-6380, 66(19).

Gardner et al., Characterization of peptidyl boronic acid inhibitors of mammalian 20 S and 26 S proteasomes and their inhibition of proteasomes in cultured cells, Biochem. J., 2000, 447-454, 346.

Collet et al., Synthesis and evaluation of ω-borono-α-amino acids as active-site probes of arginase and nitric oxide synthases, J. Chem. Soc., Perkin Trans. 1, 2000, 177-182.

Mantri et al., New Asymmetric Synthesis of α-Aminoboronic Acids Containing Functionalized Side Chains, J. Org. Chem., 1996, 5690-5692, 61(16).

Lin et al., Synthesis and properties of a novel phosphodiester analogue, nucleoside boranophosphorothioate, Chem. Commun., 1999, 1517-1518.

Shull et al., Evidence for spontaneous, reversible paracyclophane formation, Aprotic solution structure of the boron neutron capture therapy drug, L-p-boronophenylalanine, J. Chem. Soc., Perkin Trans. 2, 2000, 557-561.

Pergament et al., Arouzov Reaction of 1-Iodobornates as a Means of Preparing C1-Bridged Phosphonoboronates, Tetrahedron Letters, 1999, 3895-3898, 40.

Zhuo et al., Synthesis and Biological Evaluation of Boron-Containing Polyamines as Potential Agents for Neutron Capture Therapy of Brain Tumors, J. Med. Chem., 1999. 1282-1292, 42(7).

Soloway et al., The Chemistry of Neutron Capture Therapy, Chem. Rev., 1998, 1515-1562, 98(4).

Vogels et al., Synthesis and antifungal properties of benzylamines containing boronate esters, Can. J. Chem., 2001, 1115-1123, 79.

Gronowitz et al., Suecica, 1971, 377, 8. (not available).

Suginome et al., Regio- and stereoselective synthesis of boryl-substituted allyisllanes via transition metal-catalyzed slaboration, Journal of Organometallic Chemistry, 2003, 43-50, 880.

Da Silva et al., Regio- and stereoselective addition of sterically hindered silylboranes to terminal alkynes, Joural of Organometallic Chemistry, 2002, 179-190, 646.

Kajiwara et al., Insertion of an Overcrowded Silylene into Hydro- and Haloboranes: A Novel Synthesis of Silylborane Derivatives and Their Properties, Organometallics, 2004, 4723-4734, 23(20).

Ishiyama et al., Transltion metal-catalyzed borylation of alkanes and arenes via C-H activation, Journal of Organometallic Chemistry, 2003, 3-11, 680.

Lane et al., Catecholborane: A New Hydroboration Reagent, Tetrahedron, 1976, 981-990, vol. 32.

Pereira et al., A Study of Hydroboration of Alkenes and Alkynes with Pinacolborane Catalyzed by Transition Metals, Tetrahedron Letters, 1996, 3283-3286, 37(19).

Suginome et al., Regio- and Stereoselective Synthesis of (Z)-β-Silylalkenylboranes by Silaboration of Alkynes Catalyzed by Palladium and Platinum Complexes, Tetrahedron, 1999, 8787-8800, 55.

Nesmeyanov et al., Bimetallic derivatives of the ethylene series, Izv. Akad. Nauk SSSR, Ser. Khim. 1969, 2026-2029, 9, Columbus, OH, USA: Chemical abstracts, vol. 72, 1970, p. 331.

Tucker et al., Mild and Stereoselective Hydroborations of Functionalized Alkynes and Alkenes Using Pinacolborane, J. Org. Chem., 1992, 3482-3485, 67(12).

* cited by examiner

METHODS OF PREPARING MAIN GROUP BORYL COMPOUNDS

This application claims the benefit under 35 USC § 119(e) from U.S. provisional patent application Ser. No. 60/655,427, filed Feb. 24, 2005.

FIELD OF INVENTION

The present invention relates to an improved method for the preparation of boryl compounds, particularly the preparation of main group boryl compounds, from main group hydrides and hydroborating reagents.

BACKGROUND OF INVENTION

Main group boryl compounds have found many industrial applications, for example in the pharmaceutical and agricultural industries, as well as in specialty and solid state chemical fields. Main group boryl compounds are also remarkably useful synthetic intermediates.

Compounds containing boronic acids (RB(OH)$_2$) or boronate esters (RB(OR')$_2$) have received considerable attention in catalysed carbon-carbon bond formation reactions [(a) N. Miyaura and A. Suzuki, *Chem. Rev.* 1995, 95, 2457. (b) B. M. Trost and M. D. Spagnol, *J. Chem. Soc., Perkin Trans* 1 1995, 2083. (c) D. M. T. Chan, K. L. Monaco, R. P. Wang and M. P. Winters, *Tetrahedron Lett.* 1998, 39, 2933. (d) F. Berrée, P. Girard-Le Bleis and B. Carboni, *Tetrahedron Lett.* 2002, 43, 4935. (e) S. Sakuma and N. Miyaura, *J. Org. Chem.* 2001, 66, 8944.], solid-phase synthesis (B. Carboni, C. Pourbaix, F. Carreaux, H. Deleuze and B. Maillard, *Tetrahedron Lett.* 1999, 40, 7979.), macrocyclic chemistry (N. Farfan, H. Hopfl, V. Barba, M. E. Ochoa, R. Santillan, E. Gomez and A. Gutierrez, *J. Organomet. Chem.* 1999, 581, 70.), organometallic and organic synthesis [(a) F. Minutolo and J. A. Katzenellenbogen, *Organometallics* 1999, 18, 2519. (b) D. S. Matteson, *Tetrahedreon* 1989, 45, 1859. (c) J. Tailor and D. G. Hall, *Org. Lett.* 2000, 2, 3715. (d) N. A. Petasis and I. A. Zavialov, *J. Am. Chem. Soc.* 1998, 120, 11798. (e) R. A. Batey, D. B. MacKay and V. Santhakumar, *J. Am. Chem. Soc.* 1999, 121, 5075.] and as glucose sensors for diabetes therapy [(a) M. Yamamoto, M. Takeuchi and S. Shinkai, *Tetrahdedron*, 1998, 54, 3125. (b) H. Eggert, J. Frederiksen, C. Morin and J. Chr. Norrild, *J. Org. Chem.* 1999, 64, 3846. (c) S. Arimori, C. J. Ward and T. D. James, *Tetrahedron Lett.* 2002, 43, 303. (d) W. Wang, X. Gao and B. Wang, *Curr. Org. Chem.* 2002, 6, 1285.]. Over the years, interest in compounds containing boronic acids or boronate esters have also arisen because of the potent biological activities of these compounds [(a) T. D. James, P. Linnane and S. Shinkai, *J. Chem. Soc., Chem. Commun.* 1996, 281. (b) W. Yang, X. Gao and B. Wang, *Med. Res. Rev.* 2003, 23, 346. (c) C. Morin, *Tetrahedron* 1994, 50, 12521. (d) V. S. Stoll, B. T. Eger, R. C. Hynes, V. Martichonok, J. B. Jones and E. F. Pai, *Biochemistry* 1998, 37, 451. (e) S. J. Coutts, T. A. Kelly, R. J. Snow, C. A. Kennedy, R. W. Barton, J. Adams, D. A. Krolikowski, D. M. Freeman, S. J. Campbell, J. F. Ksiazek and W. W. Bachovchin, *J. Med. Chem.* 1996, 39, 2087. (f) E. S. Priestley and C. P. Decicco, *Org. Lett.* 2000, 2, 3095. (g) E. Skordalakes, R. Tyrell, S. Elgendy, C. A. Goodwin, D. Green, G. Dodson, M. F. Scully, J. M. H. Freyssinet, V. V. Kakkar and J. J. Deadman, *J. Am. Chem. Soc.* 1997, 119, 9935. (h) M. L. Stolowitz, C. Ahlem, K. A. Hughes, R. J. Kaiser, E. A. Kesicki, G. Li, K. P. Lund, S. M. Torkelson and J. P. Wiley, *Bioconjugate Chem.* 2001, 12, 229. (i) S. Jagannathan, T. P. Forsyth and C. A. Kettner, *J. Org. Chem.* 2001, 66, 6375. (j) R. C. Gardner, S. J. Assinder, G. Christie, G. G. F. Mason, R. Markwell, H. Wadsworth, M. Mclaughlin, R. King, M. C. Chabot-Fletcher, J. J. Breton, D. Allsop and A. J. Rivett, *Biochem. J.* 2000, 346, 447. (k) S. Collet, F. Carreaux, J. L. Boucher, S. Pethe, M. Lepoivre, R. Danion-Bougot and D. Danion, *J. Chem. Soc., Perkin Trans.* 1 2000, 177. (l) P. Mantri, D. E. Duffy and C. A. Kettner, *J. Org. Chem.* 1996, 61, 5690. (m) J. Lin and B. R. Shaw, *Chem. Commun.* 1999, 1517. (n) B. K. Shull, D. E. Spielvogel, R. Gopalaswamy, S. Sankar, P. D. Boyle, G. Head and K. Devito, *J. Chem. Soc., Perkin Trans.* 2 2000, 557. (o) I. Pergament and M. Srebnik, *Tetrahedron Lett.* 1999, 40, 3895. (p) P. R. Westmark and B. D. Smith, *J. Am. Chem. Soc.* 1994, 116, 9343.].

As an example, α-aminoboronic acids having the general formula of:

are effective and reversible inhibitors of serine proteases—a diverse group of proteoloytic enzymes whose numerous physiological functions include digestion, growth, differentiation and apoptosis. Since proteases have also been found to be vital in the generation of most disease processes, much effort has been focused on the synthesis of α-aminoboronic acids for possible applications as enzyme inhibitors.

Amino acid analogs containing boronic acids have been investigated for their use in boron neutron capture therapy (BNCT) for the treatment of cancer [(a) L. Weissfloch, M. Wagner, T. Probst, R. Senekowitsch-Schmidtke, K. Tempel and M. Molls, *Biometals* 2001, 14, 43. (b) J. Thomas and M. F. Hawthorne, *Chem. Commun.* 2001, 1884. (c) I. B. Sivaev, A. B. Bruskin, V. V. Nesterov, M. Y. Antipin, V. I. Bregadze and S. Sjöberg, *Inorg. Chem.* 1999, 38, 5887. (d) E. B. Kullberg, N. Bergstrand, J. Carlsson, K. Edwards, M. Johnsson, S. Sjöberg and L. Gedda, *Bioconjugate Chem.* 2002, 13, 737. (e) R. R. Srivastava and G. W. Kabalka, *J. Org. Chem.* 1997, 62, 8730. (f) G. W. Kabalka, B. C. Das and S. Das, *Tetrahedron Lett.* 2001, 42, 7145. (g) X. Q. Pan, H. Wang, S. Shukla, M. Sekido, D. M. Adams, W. Tjarks, R. F. Barth and R. L. Lee, *Bioconjugate Chem.* 2002, 13, 435. (h) J. Cai, A. H. Soloway, R. F. Barth, D. M. Adams, J. R. Hariharan, I. M. Wyzlic and K. Radcliffe, *J. Med. Chem.* 1997, 40, 3887. (i) J. C. Zhuo, J. Cai, A. H. Soloway, R. F. Barth, D. M. Adams, W. Ji and W. Tjarks, *J. Med. Chem.* 1999, 42, 1282. (j) A. H. Soloway, W. Tjarks, B. A. Barnum, F. G. Rong, R. F. Barth, I. M. Codogni and J. G. Wilson, *Chem. Rev.* 1998, 98, 1515.] BNCT is a bimodal form of therapy which depends on selectively depositing boron-10 atoms into the cancerous tumour prior to irradiation by slow (thermal) neutrons.

An example of an amino acid analog containing boronic acid is 4-dihydroxyborylphenylalanine (BPA):

which is a simple second generation BNCT compound, potentially useful in the treatment of brain tumours (A. H.

Soloway, W. Tjarks, B. A. Barnum, F. G. Rong, R. F. Barth, I. M. Codogni and J. G. Wilson, *Chem. Rev.* 1998, 98, 1515.).

Furthermore, recent work has found that certain boron compounds also show considerable antifungal (C. M. Vogels, L. G. Nilolcheva, H. A. Spinney, D. W. Norman, M. O. Baerlocher, F. J. Baerlocher and S. A. Westcott, *Can. J. Chem.* 2001, 79, 1115) and antibacterial activity (S. Gronowitz, T. Dalgren, J. Namtvedt, C. Roos, B. Sjöberg and U. Forsgren, *Acta Pharm. Suecica*, 1971, 8, 377). Indeed, the compound 2-formylphenylboronic acid:

is a strong fungicidal agent against both *Aspergillus niger* and *Aspergillus flavus*.

Silylboryl compounds of the general formula [$R_3SiB(XR')_2$] have also been of special interest because of their properties [(a) M. Suginome and Y. Ito, *J. Organomet Chem.* 2003, 680, 43. (b) J. C. A. Da Silva, M. Birot, J. P. Pillot and M. Pétraud, *J. Organomet. Chem.* 2002, 646, 179. (c) T. Kajiwara, N. Takeda, T. Sasamori and N. Tokitoh, *Organometallics*, 2004, 23, 4723.] A comprehensive review on the chemistry of silylboranes has recently been published (M. Suginome and Y. Ito, *J. Organomet. Chem.* 2003, 680, 43). However, despite many of the interesting properties and applications associated with silylboranes, their chemistry has not yet been fully explored, mainly due to the limited synthetic methods for the preparation of these remarkable compounds.

Traditional routes to organoborate esters are based on the alkylation of trialkylborates with organomagnesium or organolithium reagents (A. Pelter, K. Smith and H. C. Brown, *Borane Reagents*, Academic Press, London, 1998). However, these reactions usually suffer from low yields. Further, the reactions are often complicated by the formation of a mixture of either magnesium or lithium salts.

The uncatalyzed addition of hydroboranes to unsaturated hydrocarbons presents another route to organoborate esters. However, this reaction suffers from selectivity problems.

New methodologies to solve the difficulties associated with making these valuable boryl compounds will no doubt have a tremendous impact in organic synthesis and in the chemical industry. New methodologies may also provide a new class of organoboronate compounds that cannot be obtained using conventional protocols. For example, the recent report that transition metals can catalyze the borylation of alkanes and arenes via C—H bond activation has already had a tremendous impact in organic synthesis (T. Ishiyama and N. Miyaura, *J. Organomet. Chem.* 2003, 680, 3).

Thus, there remains a continued need for an efficient synthesis of main group boryl compounds that requires mild reaction conditions and provides good yields.

SUMMARY OF THE INVENTION

A new method for the preparation of main group boryl compounds under mild reaction conditions has been developed. Accordingly, the present invention relates a method of preparing main group boryl compounds of formula I by reacting of a compound of formula II with a compound of formula III in the presence of a transition metal catalyst:

wherein $R^1$ is selected from the group consisting of $C_{1-20}$alkyl, aryl, heterocyclyl and $C_{3-20}$cycloalkyl, all of which may be optionally substituted;

E is a main group element selected from the group consisting of an element from Group 14, Group 15 and Group 16 of the periodic table;

n is 1 when E is a main group element from Group 16 of the periodic table;

n is 2 when E is a main group element from Group 15 of the periodic table;

n is 3 when E is a main group element from Group 14 of the periodic table;

$R^2$ and $R^{2'}$ are each independently selected from the group consisting of $C_{1-20}$alkyl, aryl, heterocyclyl and $C_{3-20}$cycloalkyl, all of which may be optionally substituted, or $R^2$ and $R^{2'}$ are linked to form an optionally substituted monocyclic or polycyclic ring system having 4 to 20 atoms, including the B, X and X' atoms;

X and X' are each independently selected from the group consisting of O, S and $NR^3$; and $R^3$ is selected from the group consisting of H, $C_{1-10}$alkyl, aryl and $C_{3-20}$cycloalkyl.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

The present invention relates to a method of preparing a main group boryl compounds of formula I by reacting of a compound of formula II with a compound of formula III in the presence of a transition metal catalyst:

wherein
R$^1$ is selected from the group consisting of C$_{1-20}$alkyl, aryl, heterocyclyl and C$_{3-20}$cycloalkyl, all of which may be optionally substituted;
E is a main group element selected from the group consisting of an element from Group 14, Group 15 and Group 16 of the periodic table;
n is 1 when E is a main group element from Group 16 of the periodic table;
n is 2 when E is a main group element from Group 15 of the periodic table;
n is 3 when E is a main group element from Group 14 of the periodic table;
R$^2$ and R$^{2'}$ are each independently selected from the group consisting of C$_{1-20}$alkyl, aryl, heterocyclyl and C$_{3-20}$cycloalkyl, all of which may be optionally substituted, or R$^2$ and R$^{2'}$ are linked to form an optionally substituted monocyclic or polycyclic ring system having 4 to 20 atoms, including the B, X and X' atoms;
X and X' are each independently selected from the group consisting of O, S and NR$^3$; and
R$^3$ is selected from the group consisting of H, C$_{1-10}$alkyl, aryl and C$_{3-20}$cycloalkyl.

Terms and Definitions

As used herein, the terms "Group 14", "Group 15" and "Group 16" refer to the Periodic Table of the elements group labeling used by the International Union of Pure and Applied Chemistry (IUPAC). The most current version of the IUPAC Periodic Table of the Elements is presented for reference in FIG. 1.

Figure 1:
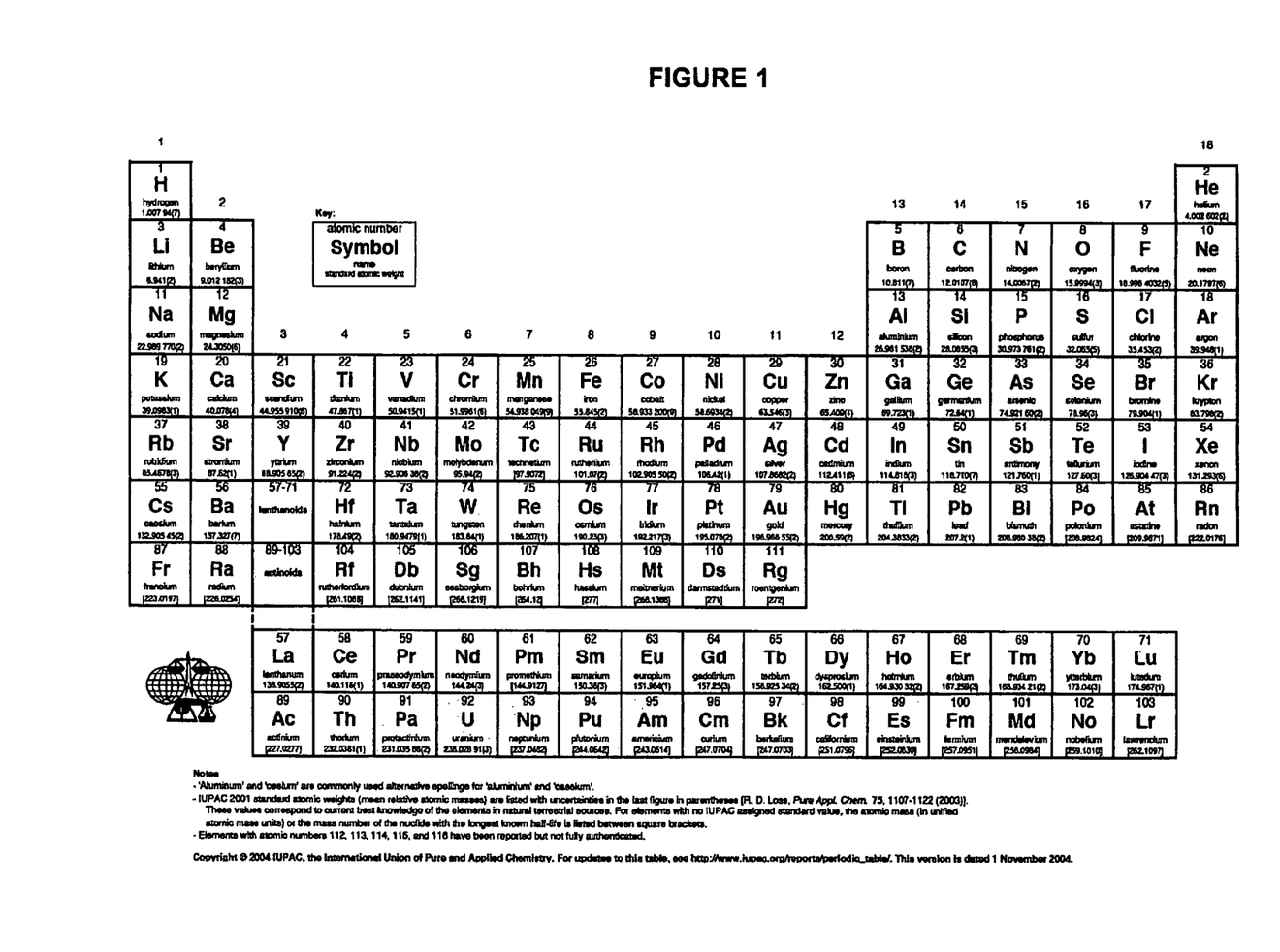
FIG. 1 is the IUPAC Period Table of the Elements as published on Nov. 1, 1994.

The term "main group" as used herein refers to the elements appearing the periods 14, 15 and 16 of the IUPAC Periodic Table of the Elements (FIG. 1).

The term "C$_{1-n}$alkyl" as used herein means straight and/or branched chain alkyl radicals containing from one to "n" carbon atoms and includes (when n=20) methyl, ethyl, n-propyl, n-butyl, n-pentyl, n-hexyl, n-heptyl, n-octyl, n-decyl, n-undecyl, n-dodecyl-, n-tridecyl, n-tetradecyl, n-pentadecyl, n-hexadecyl, n-heptadecyl, n-octadecyl, n-nonadecyl, n-icosyl and branched analogs thereof, and the like.

The term "optionally substituted C$_{1-n}$alkyl" as used herein means that the alkyl radical is either unsubstituted or substituted with one, two, three, or in the case of alkyl groups of two carbons or more, four or five substituents independently selected from the group consisting of C$_{1-4}$alkyl, OC$_{1-4}$alkyl, CF$_3$, OCF$_3$, halo, SC$_{1-4}$alkyl, NHC$_{1-4}$alkyl and N(C$_{1-4}$alkyl)(C$_{1-4}$alkyl).

The term "C$_{3-n}$cycloalkyl" as used herein means a saturated carbocylic ring or ring system containing from 3 to "n" carbon atoms and having a single ring (e.g. cyclopropyl, cyclobutyl, cyclopentyl, cyclohexyl and cycloheptyl) or multiple condensed (fused) rings (e.g. decahydronaphthalene and adamantanyl).

The term "optionally substituted C$_{3-n}$cycloalkyl" as used herein means that the C$_{3-n}$cycloalkyl radical is either unsubstituted or substituted with one, two, three, four or five substituents independently selected from the group consisting of C$_{1-4}$alkyl, OC$_{1-4}$alkyl, CF$_3$, OCF$_3$, halo, SC$_{1-4}$alkyl, NHC$_{1-4}$alkyl and N(C$_{1-4}$alkyl)(C$_{1-4}$alkyl).

The term "halo" as used herein means halogen and includes chloro, bromo, iodo and fluoro.

The term "aryl" as used herein means a monocyclic or bicyclic carbocyclic ring system containing one or two aromatic rings and from 6 to 14 carbon atoms and includes phenyl, naphthyl, anthraceneyl, 1,2-dihydronaphthyl, 1,2,3,4-tetrahydronaphthyl, fluorenyl, indanyl, indenyl and the like.

The term "optionally substituted aryl" as used herein means that the aryl radical is either unsubstituted or substituted with one, two, three, four or five substituents independently selected from the group consisting of C$_{1-4}$alkyl, OC$_{1-4}$alkyl, CF$_3$, OCF$_3$, halo, SC$_{1-4}$alkyl, NHC$_{1-4}$alkyl and N(C$_{1-4}$alkyl)(C$_{1-4}$alkyl).

The term "Ph" as used herein means phenyl.

The term "heterocyclyl" or "heterocycle" as used interchangeably herein means a 5- or 6-membered ring, unless otherwise specified, containing one, two, three, or four heteroatoms independently selected from the group consisting of nitrogen, oxygen and sulfur. The 5-membered ring has zero or two double bonds and the 6-membered ring has zero or three double bonds. The term "heterocyclyl" or "heterocycle" also includes bicyclic groups in which any of the above heterocyclic rings is fused to one or two rings independently selected from the group consisting of an aryl ring, a cyclohexane ring, a cyclopentane ring, and another monocyclic heterocyclic ring and includes indolyl, quinolyl, isoquinolyl, tetrahydroquinolyl, benzofuryl, benzothienyl and the like. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, tetrahydrothienyl, dihydroinidolyl, tetrahydroquinolyl, tetrahydroisoquinolyl, pyranyl, dithiazolyl, benzofuranyl, benzothienyl and the like. Heterocyclic groups also include compounds of the formula where F' is selected from the group consisting of —CH$_2$—, —CH$_2$O— and —O—, and G' is selected from the group consisting of —C(O)— and —(C(R')(R''))$_v$—, where each of R' and R'' is, independently, selected from the group consisting of hydrogen or C$_{1-4}$alkyl, and v is one, two or three and includes groups such as 1,3-benzodioxolyl, 1,4-benzodioxanyl and the like.

The term "optionally substituted heterocyclyl" or "optionally substituted heterocycle" as used interchangeably herein means a heterocyclyl radical or heterocycle that is either unsubstituted or substituted with one, two, three, four or five substituents independently selected from the group consisting of $C_{1-4}$alkyl, $OC_{1-4}$alkyl, $CF_3$, $OCF_3$, halo, $SC_{1-4}$alkyl, $NHC_{1-4}$alkyl and $N(C_{1-4}alkyl)(C_{1-4}alkyl)$.

When $R^2$ and $R^{2'}$ are linked together to form one or more rings, said rings may contain five or more carbon atoms, suitably five to twenty carbon atoms, having a single ring structure or multiple condensed (fused) ring structure. Further, in the rings, one or more, suitably one or two, more suitably one, of the carbon atoms may be substituted with a heteroatom selected from O, S, N, P and Si, which, where possible, is optionally substituted with H or $C_{1-4}$alkyl. Still further, the rings may be unsubstituted or substituted with one, two, three, four or five substituents independently selected from the group consisting of $C_{1-4}$alkyl, $OC_{1-4}$alkyl, $CF_3$, $OCF_3$, halo, $SC_{1-4}$alkyl, $NHC_{1-4}$alkyl and $N(C_{1-4}alkyl)(C_{1-4}alkyl)$.

It is understood that substituents and substitution patterns on the compounds of Formula I, II or III can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "optionally substituted with at least one substituent" and in such cases a specific embodiment will have from zero to four substituents.

In the method of preparing the main group boryl compounds of the formula I of the present invention, E in formulae I and II is a main group element selected from the group consisting of an element from Group 14, Group 15 and Group 16 of the periodic table and n is 1 when E is a main group element from Group 16 of the periodic table, n is 2 when E is a main group element from Group 15 of the periodic table and n is 3 when E is a main group element from Group 14 of the periodic table. In embodiments of the invention E is selected from the group consisting of S, Se, Te, P, As, Sb, Si, Ge and Sn. In still further embodiments of the invention E is selected from the group consisting of S, Se, Si, Ge and Sn.

According to the present invention, $R^1$ in the compounds of the formulae I and II is selected from the group consisting of $C_{1-20}$alkyl, aryl, heterocyclyl and $C_{3-20}$cycloalkyl, all of which may be optionally substituted. In embodiments of the invention, $R^1$ in the compounds of the formulae I and II is selected from the group consisting of $C_{1-10}$alkyl or optionally substituted aryl. More particularly, $R^1$ in the compounds of the formulae I and II is selected from the group consisting of $C_{1-6}$alkyl or optionally substituted phenyl. Still more specifically, $R^1$ in the compounds of the formulae I and II is selected from the group consisting of methyl, ethyl, n-propyl, i-propyl, i-butyl, t-butyl, n-butyl, phenyl and methylphenyl. Even more specifically, $R^1$ in the compounds of the formulae I and II is selected from the group consisting of methyl, ethyl, n-butyl, phenyl and 4-methylphenyl When $R^1$ in the compounds of the formulae I and II is substituted, the substituents are independently selected from one or more, suitably one to four, more suitably one or two, even more suitably one, of $C_{1-4}$alkyl, $OC_{1-4}$alkyl, $CF_3$, $OCF_3$, halo, $SC_{1-4}$alkyl, $NHC_{1-4}$alkyl and $N(C_{1-4}alkyl)(C_{1-4}alkyl)$. In embodiments of the invention, the substituents on $R^1$ are selected from one or more, suitably one to four, more suitably one or two, even more suitably one, of $CH_3$, $OCH_3$, $CF_3$, $OCF_3$, Cl, F, Br, $SCH_3$, $NHCH_3$ and $N(CH_3)_2$. In further embodiments of the invention, the substituents on $R^1$ are selected from one or more, suitably one to four, more suitably one or two, even more suitably one, of $CH_3$ and F.

The invention also includes compounds of the formulae I and III where $R^2$ and $R^{2'}$ are each independently selected from the group consisting of $C_{1-20}$alkyl, aryl, heterocyclyl and $C_{3-20}$cycloalkyl, all of which may be optionally substituted, or $R^2$ and $R^{2'}$ are linked to form an optionally substituted monocyclic or polycyclic ring system having 4 to 20 atoms, including the B, X and X' atoms. In embodiments of the invention, $R^2$ and $R^{2'}$ in the compounds of formulae I and III are each independently selected from the group consisting of $C_{1-10}$alkyl, aryl, heterocyclyl and $C_{3-10}$cycloalkyl, all of which may be optionally substituted, or $R^2$ and $R^{2'}$ are linked to form an optionally substituted monocyclic or polycyclic ring system having 4 to 9 atoms, including the B, X and X' atoms to which $R^2$ and $R^{2'}$ are bonded. In further embodiments of the invention, $R^2$ and $R^{2'}$ in the compounds of formulae I and III are each independently selected from the group consisting of $C_{1-6}$alkyl, phenyl, and $C_{3-6}$cycloalkyl, or $R^2$ and $R^{2'}$ are linked to form an optionally substituted monocyclic or polycyclic ring system having 4 to 9 atoms, including the B, X and X' atoms. In still further embodiments of the invention $R^2$ and $R^{2'}$ in the compounds of formulae I and III are linked to form an optionally substituted monocyclic or polycyclic ring system having 5 to 9 atoms, including the B, X and X' atoms. In even further embodiments of the invention $R^2$ and $R^{2'}$ in the compounds of formulae I and III are linked to form an optionally substituted 5-membered monocylic ring or an optionally substituted 5-membered monocylic ring fused to a phenyl ring. In embodiments of the invention, the optional substituents on $R^2$ and $R^{2'}$ are one or more $C_{1-4}$alkyl groups, suitably 1, 2, 3 or 4 $C_{1-4}$alkyl groups, more suitably 1, 2, 3 or 4 methyl groups. In further embodiments of the invention $R^2$ and $R^{2'}$ including the B, X and X' atoms and optional substituents combine to form a catecholboryl or pinacolboryl group.

In the monocyclic or polycyclic ring system formed by $R^2$ and $R^{2'}$ in the compounds of formulae I and III, the system may include one or more, suitably one or two, more suitably one, heteroatoms (aside from B, X and X') selected from O, S, N, P and Si, which, where possible, are optionally substituted with H or $C_{1-4}$alkyl, suitably H or $CH_3$. In embodiments of the invention, the monocyclic or polycyclic ring system formed by $R^2$ and $R^{2'}$ in the compounds of formulae I and III may include one or more, suitably one or two, more suitably one, heteroatoms (aside from B, X and X') selected from O, S, and N, which, where possible, are optionally substituted with H or $C_{1-4}$alkyl, suitably H or $CH_3$. In still further embodiments of the invention the monocyclic or polycyclic ring system formed by $R^2$ and $R^{2'}$ in the compounds of formulae I and III includes no heteroatoms aside from B, X and X'.

According to the present invention, X and X' in the compounds of the formulae I and III are each independently selected from the group consisting of O, S and $NR^3$, wherein $R^3$ is H, $C_{1-10}$alkyl, aryl or $C_{3-20}$cycloalkyl. In embodiments X and X' in the compounds of the formulae I and III are each independently selected from the group consisting of O, S, $NCH_3$ and N—Ph. In still further embodiments of the invention X and X' in the compounds of the formulae I and III are each O.

In the method of the present invention, the transition metal catalyst includes transition metal salts and complexes of transition metal salts thereof, which may be, for example, $PdCl_2$, $PdBr_2$, $PdI_2$, $Na_2PdCl_4$, $PdCl_2(PPh_3)_2$, $Pd(PPh_4)_3$, $RhCl(PPh_3)_3$, $Rh(acac)(P2)$, wherein acac is acetylacetonato and P2 represents two monodentate phosphine ligands or one bidentate phosphine ligand, $Rh(acac)(L2)$, wherein acac is acetylacetonato and L represents a bidentate or two monodentate Lewis basic ligands. The Lewis basic ligands may be selected from, for example, imines, amines, pyridines and carbenes. In specific embodiments of the invention, the transition metal catalyst is selected from $PdCl_2$, $PdBr_2$, $PdI_2$, $Na_2PdCl_4$, $PdCl_2(PPh_3)_2$, $Pd(PPh_3)_4$, $RhCl(PPh_3)_3$, $Rh(acac)(P2)$, wherein acac is acetylacetonato and P2 represents two monodentate phosphine ligands or one bidentate phosphine ligand.

In embodiments of the invention, the process is performed in an inert organic solvent. More particularly, the organic solvent is selected from toluene, tetrahydrofuran, acetonitrile, benzene, methylene chloride. Still more particularly, the organic solvent is toluene.

In embodiments of the invention, the main group hydride of the formula II is selected from the group consisting of 4-methylbenzenethiol, benzeneselenol, triphenylsilane, triphenyltin hydride, tributyltin hydride, and triphenylgermanium hydride.

Still further, in embodiments of the invention, the hydroborating reagent of the formula III is selected from the group consisting of pinacolborane and catecholborane.

Compounds of Formulae II and III and the transition metal catalysts are either commercially available or may be prepared using procedures well known in the art. For example, main group hydrides may be prepared as described in *Inorg. Syntheses*, Ed. M. Y. Darensbourg, John Wiley & Sons Canada Ltd., Toronto, vol. 32, 1998), catecholborane may be prepared as described in C. F. Lane and G. W. Kabalka, *Tetrahedron* 1976, 32, 981 and A. Pelter, K. Smith and H. C. Brown, *Borane Reagents*; Academic Press, New York, 1988) and pinacolborane may be prepared as described in S. Pereira and M. Srebnik, *Tetrahedron Lett.* 1996, 37, 3283 and C. E. Tucker, J. Davidson and P. Knochel, *J. Org. Chem.*, 1992, 57, 3482.

EXAMPLES

The following non-limiting examples are illustrative of the present invention.

Materials and Instrumentations: Reagents and solvents used were purchased from Aldrich Chemicals. The transition metal catalysts used were $PdCl_2$, $PdBr_2$, $PdI_2$, $Na_2PdCl_4$, $PdCl_2(PPh_3)_2$, $Pd(PPh_3)_4$, $RhCl(PPh_3)_3$ and $Rh(acac)(P2)$, in which acac is acetylacetonato and P2 represents two monodentate phosphine ligands or one bidentate phosphine ligand. NMR spectra were recorded on a JEOL JNM-GSX270 FT spectrometer. $^1H$ NMR chemical shifts are reported in ppm and referenced to residual solvent protons in deuterated solvent at 270 MHz. $^{11}B$ NMR chemical shifts are reported in ppm and are referenced to $BF_3 \cdot OEt_2$ as an external standard at 87 MHz. $^{13}C$ NMR chemical shifts are referenced to solvent carbon resonances as internal standards at 68 MHz and are reported in ppm. Mutiplicities are reported as singlet (s), doublet (d), multiplet (m), and overlapping (ov). All experiments were conducted under an atmosphere of dinitrogen in a MBraun UNIlab glovebox.

Example 1

Synthesis of (4-methylphenylthio)pinacolborane

To a toluene solution of 4-methylbenzenethiol and 1 mol % of catalyst, 1 equivalent of pinacolborane was added. After 18 hours, the solvent was removed under vacuum and the product was recrystallized from diethylether at −30° C. Spectroscopic NMR data $(C_6D_6)$: $^1H$ δ:7.57 (d, J=8 Hz, 2H, Ar), 6.83 (d, J=8 Hz, 2H, Ar), 1.94 (s, 3H, $CH_3$), 0.97 (s, 12H, $O_2C_2(CH_3)_4$); $^{11}B\{^1H\}$ δ:32.4; $^{13}C\{^1H\}$ δ:136.5, 133.6, 129.6, 126.5, 84.8, 24.2. 20.6.

Figure 2:
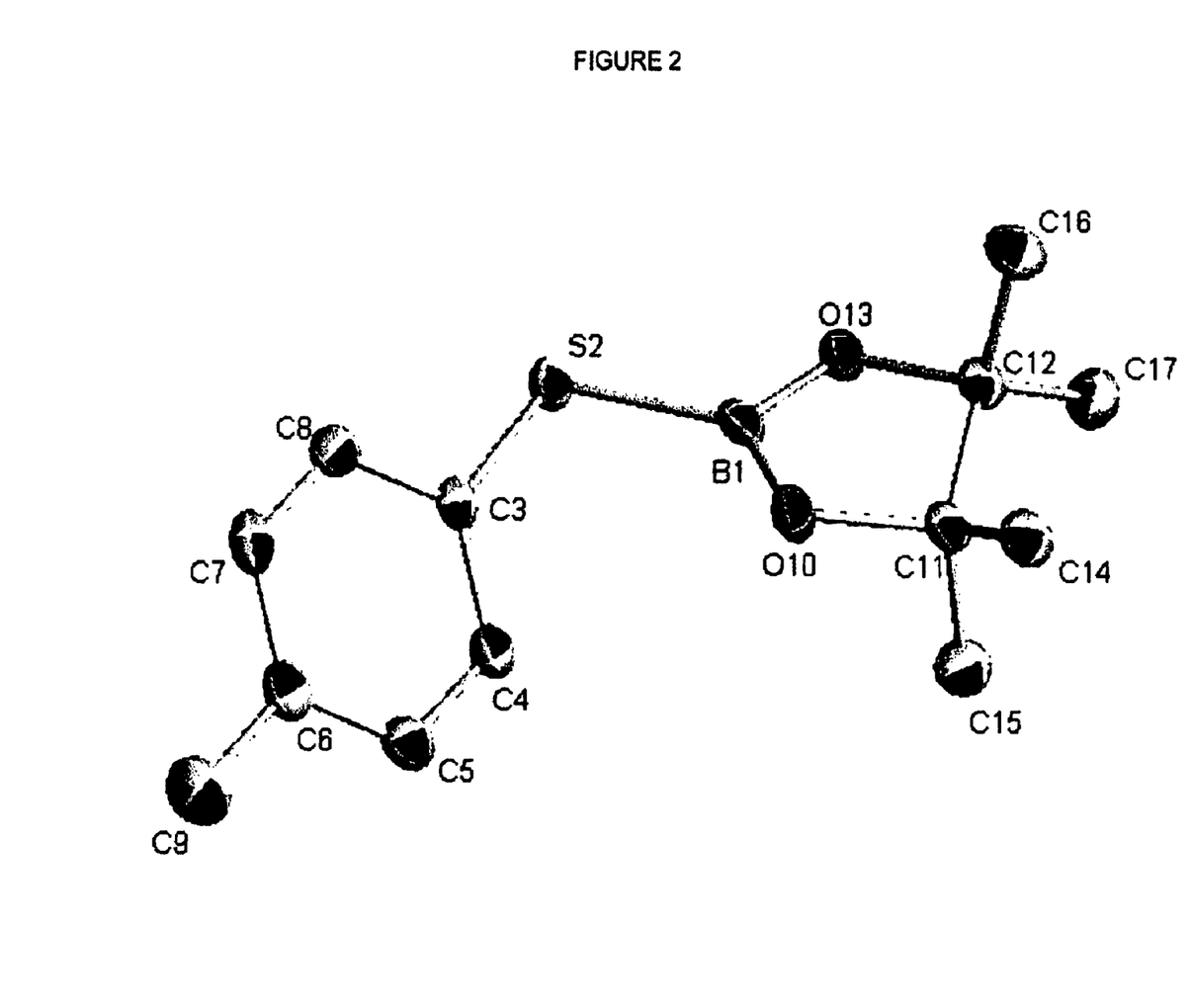
FIG. 2 is the crystal structure of compound (4-methylphenylthio)pinacolborane as determined by x-ray diffraction.

The crystal structure of the final compound was determined by x-ray diffraction, and is shown in FIG. 2. Single crystals suitable for x-ray diffraction studies were grown from a hexane solution at −5° C. Single crystals were coated with Paratone-N oil, mounted using a glass fibre and frozen in the cold stream of the goniometer. A hemisphere of data were collected on a Bruker AXS P4/SMART 1000 diffractometer with a scan width of 0.3 degrees and 10 seconds exposure times. The detector distances was 6 cm. The data were reduced [as described in SAINT 6.02, Bruker AXS, Inc., Madison, Wis., USA. (1997-1999)] and corrected for absorption [as described by G. M. Sheldrick, SADABS, Bruker AXS, Inc., Madison, Wis., USA. (1999)]. The structures were solved by direct methods and refined by full-matrix least squares on F2 [as described by G. M. Sheldrick, SHELXTL 5.1, Bruker AXS, Inc., Madison, Wis., USA. (1997)]. All non-hydrogen atoms were refined anisotropically. Hydrogen atoms were located in Fourier difference maps and refined isotropically.

Example 2

Synthesis of (phenylselenyl)pinacolborane

To a toluene solution of benzeneselenol and 1 mol % of catalyst, 1 equivalent of pinacolborane was added. After 18 hours, the solvent was removed under vacuum and the product was recrystallized from diethylether at −30° C. Spectroscopic NMR data $(C_6D_6)$: $^1H$ δ:7.74 (d, J=8 Hz, 2H, Ar), 6.98-6.93 (ov m, 3H, Ar), 0.96 (s, 12H, $O_2C_2(CH_3)_4$); $^{11}B\{^1H\}$ δ:33.4; $^{13}C\{^1H\}$ δ:134.8, 128.9, 126.8, 125.2, 85.2, 24.2.

Example 3

Synthesis of (triphenylsilyl)pinacolborane

To a toluene solution of triphenylsilane and 5 mol % of catalyst, 3 equivalents of pinacolborane was added. The mixture was heated to reflux for 24 hours, at which point the solvent was removed and spectroscopic NMR data was collected. Spectroscopic NMR data ($C_6D_6$): $^{11}B\{^1H\}$ δ:30.3.

Example 4

Synthesis of (triphenyltin)pinacolborane

To a toluene solution of triphenyltin hydride and 5 mol % of catalyst, 3 equivalents of pinacolborane was added. The mixture was heated to reflux for 24 hours, at which point the solvent was removed and spectroscopic NMR data was collected. Spectroscopic NMR data ($C_6D_6$): $^{11}B\{^1H\}$ δ:30.5.

Example 5

Synthesis of (tributyltin)pinacolborane

To a toluene solution of tributyltin hydride and 5 mol % of catalyst, 1 equivalent of pinacolborane was added. The mixture was heated to reflux for 24 hours, at which point the solvent was removed and spectroscopic NMR data was collected. Spectroscopic NMR data ($C_6D_6$): $^{11}B\{^1H\}$ δ:33.9.

Example 6

Synthesis of (triphenylgermanium)pinacolborane

To a toluene solution of triphenylgermanium hydride and 5 mol % of catalyst, 3 equivalents of pinacolborane was added. The mixture was heated to reflux for 24 hours, at which point the solvent was removed and spectroscopic NMR data was collected. Spectroscopic NMR data ($C_6D_6$): $^{11}B\{^1H\}$ δ:30.3.

Example 7

Synthesis of (4-methylphenylthio)catecholborane

To a toluene solution of 4-methylbenzenethiol and 1 mol % of catalyst, 1 equivalent of catecholborane was added. The mixture was heated to reflux for 24 hours, at which point the solvent was removed and spectroscopic NMR data was collected. Spectroscopic NMR data ($C_6D_6$): $^1H$ δ:7.39 (d, J=8 Hz, 2H, Ar), 6.91-6.86 ($2^{nd}$ order m, 2H, Bcat), 6.82 (d, J=8 Hz, 2H, Ar), 6.73-6.68 ($2^{nd}$ order m, 2H, Bcat), 1.94 (s, 3H, $CH_3$); $^{11}B\{^1H\}$ δ:34.3.

Example 8

Synthesis of (phenylselenyl)catecholborane

To a toluene solution of benzeneselenol and 1 mol % of catalyst, 1 equivalent of catecholborane was added. After 18 hours, the solvent was removed and spectroscopic NMR data was collected. Spectroscopic NMR data ($C_6D_6$): $^{11}B\{^1H\}$ δ:35.3.

Example 9

Synthesis of (triphenylsilyl)catecholborane

To a toluene solution of triphenylsilane and 1 mol % of catalyst, 1.5 equivalents of catecholborane was added. The mixture was heated to reflux for 24 hours, at which point the solvent was removed and spectroscopic NMR data was collected. Spectroscopic NMR data ($C_6D_6$): $^{11}B\{^1H\}$ δ:31.7.

Example 10

Synthesis of (triphenyltin)catecholborane

To a toluene solution of triphenyltin hydride and 5 mol % of catalyst, 1.5 equivalents of catecholborane was added. After 18 hours, the solvent was removed and spectroscopic NMR data was collected. Spectroscopic NMR data ($C_6D_6$): $^{11}B\{^1H\}$ δ:31.2.

Example 11

Synthesis of (tributyltin)catecholborane

To a toluene solution of tributyltin hydride and 5 mol % of catalyst, 1.5 equivalents of catecholborane was added. After 18 hours, the solvent was removed and spectroscopic NMR data was collected. Spectroscopic NMR data ($C_6D_6$): $^{11}B\{^1H\}$ δ:34.3.

Example 12

Synthesis of (triphenylgermanium)catecholborane

To a toluene solution of triphenylgermanium hydride and 5 mol % of catalyst, 3 equivalents of catecholborane was added. The mixture was heated to reflux for 24 hours, at which point the solvent was removed and spectroscopic NMR data was collected. Spectroscopic NMR data ($C_6D_6$): $^1H$ δ:8.10-8.05 (m, 2H, Ar), 7.20-7.12 (ov m, 3H, Ar), 7.08-7.03 ($2^{nd}$ order m, 2H, Bcat), 6.82-7.76 ($2^{nd}$ order m, 2H, Bcat); $^{11}B\{^1H\}$ δ:31.5.

Example 13

Conversion of 4-methylbenzenethiol to (4-methylphenylthio)pinacolborane and Conversion of 4-methylbenzenethiol to (4-methylphenylthio)catecholborane Using Various Catalysts

A comparision of the yields obtained from the conversion of 4-methylbenzenethiol to (4-methylphenylthio)pinacolborane and the conversion of 4-methylbenzenethiol to (4-methylphenylthio)catecholborane using various catalysts is shown in Table 1.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Conversion of 4-methylbenzenethiol to (4-methylphenylthio)pinacolborane and conversion of 4-methylbenzenethiol to (4-methylphenylthio)catecholborane using various catalysts

| Catalyst | Yield[c] (%) pinacolborane | Yield[c] (%) Catecholborane |
|---|---|---|
| RhCl(PPh₃)₃ | 99[a] | 65[a] |
| RhH(PPh₃)₄ | 99[a] | 50[a] |
| Rh(acac)(dppm) | 99[a] | 50[a] |
| Rh(acac)(dppe) | 99[a] | 65[a] |
| Rh(acac)(dppp) | 99[a] | 50[a] |

TABLE 1-continued

Conversion of 4-methylbenzenethiol to (4-methylphenylthio)pinacolborane and conversion of 4-methylbenzenethiol to (4-methylphenylthio)catecholborane using various catalysts

| Catalyst | Yield[c] (%) pinacolborane | Yield[c] (%) Catecholborane |
|---|---|---|
| Rh(acac)(dppb) | 99[a] | 50[a] |
| PdCl$_2$ | 99[b] | 90[b] |
| PdI$_2$ | 99[b] | 95[b] |
| PdCl$_2$(PPh$_3$)$_2$ | 99[b] | 90[b] |
| Pd(PPh$_3$)$_4$ | 99[b] | 90[b] |

[a]1 mol% of catalyst, 1.1 equivalents of HBR$_2$, C$_6$D$_6$, RT, 24 hours.
[b]1 mol% of catalyst, 3 equivalents of HBR$_2$, toluene, heat 24 hours.
[c]Yield determined by $^1$H NMR spectroscopy.

We claim:

1. A method of preparing main group boryl compounds of formula I comprising reacting a compound of formula II with compound of formula III in the presence of a transition metal catalyst:

wherein
R$^1$ is selected from the group consisting of C$_{1-20}$alkyl, aryl, heterocyclyl and C$_{3-20}$cycloalkyl, all of which may be optionally substituted;
E is a main group element selected from the group consisting of S, Se, Te, P, As, Sb, Si, Ge and Sn;
n is 1 when E is S, Se or Te;
n is 2 when E is P, As or Sb;
n is 3 when E is Si, Ge or Sn;

R$^2$ and R$^{2'}$ are each independently selected from the group consisting of C$_{1-20}$alkyl, aryl, heterocyclyl and C$_{3-20}$cycloalkyl, all of which may be optionally substituted, or R$^2$ and R$^{2'}$ are linked to form an optionally substituted monocyclic or polycyclic ring system having 4 to 20 atoms, including the B, X and X' atoms;

X and X' are each independently selected from the group consisting of O, S and NR$^3$; and R$^3$ is selected from the group consisting of H, C$_{1-10}$alkyl, aryl and C$_{3-20}$cycloalkyl.

2. The method according to claim 1, wherein E is selected from the group consisting of S, Se, Si, Ge and Sn.

3. The method according to claim 1, wherein R$^1$ in the compounds of the formulae I and II is selected from the group consisting of C$_{1-10}$alkyl or optionally substituted aryl.

4. The method according to claim 3, wherein R$^1$ in the compounds of the formulae I and II is selected from the group consisting of C$_{1-6}$alkyl or optionally substituted phenyl.

5. The method according to claim 4, wherein R$^1$ in the compounds of the formulae I and II is selected from the group consisting of n-butyl, phenyl and methylphenyl.

6. The method according to claim 1, wherein the optional substituents on R$^1$ in the compounds of the formulae I and II are independently selected from one to four of C$_{1-4}$alkyl, OC$_{1-4}$alkyl, CF$_3$, OCF$_3$, halo, SC$_{1-4}$alkyl, NHC$_{1-4}$alkyl and N(C$_{1-4}$alkyl)(C$_{1-4}$alkyl).

7. The method according to claim 6, wherein the optional substituents on R$^1$ are selected from one to four of CH$_3$, OCH$_3$, CF$_3$, OCF$_3$, Cl, F, Br, SCH$_3$, NHCH$_3$ and N(CH$_3$)$_2$.

8. The method according to claim 7, wherein the optional substituents on are independently selected from one to four of CH$_3$ and F.

9. The method according to claim 8, wherein the optional substituents on R$^1$ are independently selected from one of CH$_3$ and F.

10. The method according to claim 1, wherein R$^1$ is unsubstituted.

11. The method according to claim 1, wherein R$^2$ and R$^{2'}$ in the compounds of formulae I and III are each independently selected from the group consisting of C$_{1-10}$alkyl, aryl, heterocyclyl and C$_{3-10}$cycloalkyl, all of which may be optionally substituted, or R$^2$ and R$^{2'}$ are linked to form an optionally substituted monocyclic or polycyclic ring system having 4 to 9 atoms, including the B, X and X' atoms to which R$^2$ and R$^{2'}$ are bonded.

12. The method according to claim 11, wherein R$^2$ and R$^{2'}$ in the compounds of formulae I and III are each independently selected from the group consisting of C$_{1-6}$alkyl, phenyl, and C$_{3-6}$cycloalkyl, or R$^2$ and R$^{2'}$ are linked to form an optionally substituted monocyclic or polycyclic ring system having 4 to 9 atoms, including the B, X and X' atoms.

13. The method according to claim 12, wherein R$^2$ and R$^{2'}$ in the compounds of formulae I and III are linked to form an optionally substituted monocyclic or polycyclic ring system having 5 to 9 atoms, including the B, X and X' atoms.

14. The method according to claim 13, wherein R$^2$ and R$^{2'}$ in the compounds of formulae I and III are linked to form an optionally substituted 5-membered monocylic ring or an optionally substituted 5-membered monocylic ring fused to a phenyl ring.

15. The method according to claim 1, wherein the optional substituents on R$^2$ and R$^{2'}$ are 1, 2, 3 or 4 C$_{1-4}$alkyl groups.

16. The method according to claim 15, wherein the optional substituents on $R^2$ and $R^{2'}$ are 1, 2, 3 or 4 methyl groups.

17. The method according to claim 1, wherein $R^2$ and $R^{2'}$ including the B, X and X' atoms and optional substituents, combine to form a catecholboryl or pinacolboryl group.

18. The method according to claim 1, wherein X and X' in the compounds of the formulae I and III are each independently selected from the group consisting of O, S, $NCH_3$ and N-Ph.

19. The method according to claim 18, wherein X and X' in the compounds of the formulae I and III are each O.

20. The method according to claim 1, wherein the transition metal catalyst is selected from the group consisting of $PdCl_2$, $PdBr_2$, $PdI_2$, $Na_2PdCl_4$, $PdCl_2(PPh_3)_2$, $Pd(PPh_4)_3$, $RhCl(PPh_3)_3$, Rh(acac)(P2), and Rh (acac)(L2), wherein acac is acetylacetonato, P2 represents two monodentate phosphine ligands or one bidentate phosphine ligand and L2 represents one bidentate Lewis basic ligand or two monodentate Lewis basic ligands.

21. The method according to claim 1, wherein the method is performed in an organic solvent.

22. The method according to claim 21, wherein the organic solvent is selected from the group consisting of toluene, tetrahydrofuran, acetonitrile, benzene, methylene chloride.

23. The method according to claim 22, wherein the organic solvent is toluene.

24. The method according to claim 1, wherein the compound of formula II is selected from the group consisting of 4-methylbenzenethiol, benzeneselenol, triphenylsilane, triphenyltin hydride, tributyltin hydride, and triphenylgermanium hydride.

25. The method according to claim 1, wherein the compound of formula III is selected from the group consisting of pinacolborane and catecholborane.

* * * * *